(12) United States Patent
Berry

(10) Patent No.: US 11,771,473 B2
(45) Date of Patent: Oct. 3, 2023

(54) POLYAXIAL PEDICLE SCREW

(71) Applicant: Phoenyx Spinal Technologies, Inc., Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 17/665,146

(22) Filed: Feb. 4, 2022

(65) Prior Publication Data
US 2023/0248396 A1 Aug. 10, 2023

(51) Int. Cl.
*A61B 17/70* (2006.01)
(52) U.S. Cl.
CPC ........ *A61B 17/7032* (2013.01); *A61B 17/704* (2013.01); *A61B 17/7037* (2013.01)
(58) Field of Classification Search
CPC ............ A61B 17/7032; A61B 17/7035; A61B 17/7037; A61B 17/7038; A61B 17/7046; A61B 17/7049
See application file for complete search history.

(56) References Cited

U.S. PATENT DOCUMENTS

| | | | |
|---|---|---|---|
| 8,998,960 B2 | 4/2015 | Jackson | |
| 9,743,957 B2 | 8/2017 | Jackson | |
| 10,130,395 B2 | 11/2018 | Leff et al. | |
| 2007/0055244 A1* | 3/2007 | Jackson | A61B 17/864 606/86 A |
| 2008/0132957 A1* | 6/2008 | Matthis | A61B 17/8685 606/301 |
| 2013/0053901 A1* | 2/2013 | Cormier | A61B 17/7032 606/305 |
| 2017/0049482 A1* | 2/2017 | Campbell | A61B 17/7038 |
| 2017/0086895 A1* | 3/2017 | Barra | A61B 17/8605 |
| 2018/0221162 A1* | 8/2018 | Baynham | A61B 17/7037 |
| 2018/0243009 A1* | 8/2018 | Bobbitt | A61B 17/705 |

OTHER PUBLICATIONS

International Search Report and Written Opinion, issued on PCT Patent Application No. PCT/US2023/012339, dated Apr. 6, 2023.

* cited by examiner

*Primary Examiner* — Ellen C Hammond
(74) *Attorney, Agent, or Firm* — McCarter & English, LLP; James M. Smedley; Alex Korona

(57) ABSTRACT

The present invention is directed at a polyaxial pedicle screw comprising a detachable polyaxial head and bone screw. The detachable polyaxial head may comprise a tulip head, a collet with one or more connectors (e.g., pins) to secure it, and a spherical locking member which may lock onto the bone screw.

20 Claims, 11 Drawing Sheets

POLYAXIAL PEDICLE SCREW

FIELD OF INVENTION

The present invention generally relates pedicle screws. Specifically, embodiments of the present invention are directed at polyaxial pedicle screws which may comprise a bone screw and a polyaxial head assembly comprising a tulip head, a collet, and one or more connectors (e.g., pins) to secure the collet to the tulip head, and a joint configured as a substantially spherical locking member which may lock onto the bone screw.

BACKGROUND

Polyaxial pedicle screws have been used for decades to help fixate and fuse portions of the spine. For a variety of reasons, some of these polyaxial screws have had a detachable head. Inasmuch, numerous different locking mechanisms have been utilized to secure a detachable head to a bone screw. However, these have been shown to have drawbacks. Some prior-developed mechanisms disrupt the polyaxial movement by having threads or other features on the spherical portion meant for rotation. Some of the prior-developed mechanisms use overly complex mechanisms which can lead to failure in the body. Others employ an overly simplistic locking mechanism which may lead to unintended movement, detachment or disassembly while in the body. What is needed is a mechanism which is simple and straightforward to attach, but which still allows for polyaxial movement of the head once it is attached, but before it is locked. Furthermore, such a device may be configured to create rigid fixation once it has been locked.

PRIOR ART DISCUSSION

Various devices in the prior art have been developed, each of which has its drawbacks. For example, U.S. Pat. No. 10,130,395, entitled Modular Uniplanar Pedicle Screw Assembly For Use With A Polyaxial Bone Fastened, discloses a bone screw formed with a spherical head and a detachable polyaxial head which is configured to thread onto the spherical head of the bone screw. Although the polyaxial head uses a thread to attach to the bone screw, it is the head of the bone screw which has the spherical portion. This device has several drawbacks, including difficulty threading the spherical form of the polyaxial head onto the spherical form of the head of the bone screw. In certain scenarios, this configuration may require a single thread to be engaged at any one time, which can lead to misalignment. Further, the threads, once engaged, may prevent the rotation of the polyaxial head about the bone screw, making it no longer polyaxial. Moreover, the means of locking the two components is insufficient for securely locking the two components after implantation. Therefore, in some scenarios, it is possible for the threads of this device to unscrew in situ. In some scenarios, the present disclosure differs from such a device as the spherical portion may form part of the polyaxial head assembly to avoid these and similar issues.

In another example, the device disclosed in U.S. Pat. No. 8,998,960, entitled Polyaxial Bone Screw With Helically Wound Capture Connection, has a spherical member made part of the poly axial head. However, the spherical portion of this device is not truly captured within the head, and could potentially be pushed out, or fall out. For example, the internal threaded portion of the spherical member disclosed in U.S. Pat. No. 8,998,960 threads onto a bone screw, however, only friction between the spherical member against the collar of the device is utilized to "lock" the spherical member in place, and, since the spherical member is not expandable, the configuration does not sufficiently prevent against the spherical member unthreading from the bone screw in situ and partially or completely disengaging or disassembling the device. This configuration may differ from the present invention in a few aspects, including, for example, that the present invention may be provided with one or more connection members configured to secure the pedicle screw collet into place to secure the locking ball between the collet and an internal base of the tulip head and/or that the locking ball may comprise an expandable aperture comprising one or more locking tab members configured to support expansion of the expandable aperture and to engage with bone screw protruding tabs to prevent the locking ball from unthreading and/or completely disengaging from the bone screw in situ.

Another example, disclosed in U.S. Pat. No. 9,743,957, entitled Polyaxial Bone Screw With Shank Articulation Pressure Insert And Method, is similar to U.S. Pat. No. 8,999,960 described above, except a collet is added to retain the spherical member. However, this configuration lacks, for example, a locking member with an expandable aperture and/or locking tabs configured to lock with respect to the bone screw upon engagement of the locking member locking tabs and the bone screw locking tabs to prevent unthreading of the spherical member from the bone screw.

BRIEF DESCRIPTION

In accordance with embodiments of the present invention, a detachable polyaxial pedicle screw may comprise a tulip head assembly and a bone screw. The tulip head assembly may be comprised of a tulip head, a collet, a locking ball, and one or more connection members (e.g., pins). The collet may be held within (e.g., secured to) the tulip head by one or more connection members or pins. The collet may be configured to slide axially within the tulip head. Similarly, the collet may capture the locking ball within the tulip head by sandwiching the locking ball between the collet and a bottom portion of the tulip head. The locking ball may be configured to rotate polyaxially within the tulip head. The locking ball may comprise internal threads, and one or more locking tabs. A top portion of the bone screw may have threads configured to mate with internal threads of the locking ball and may further comprise one or more locking tabs. This may permit the locking ball to thread onto the top portion of the bone screw, and then securely lock onto the bone screw upon engagement of the bone screw locking tabs with the locking ball locking tabs.

BRIEF DESCRIPTION OF DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED DESCRIPTION

Figure 1:
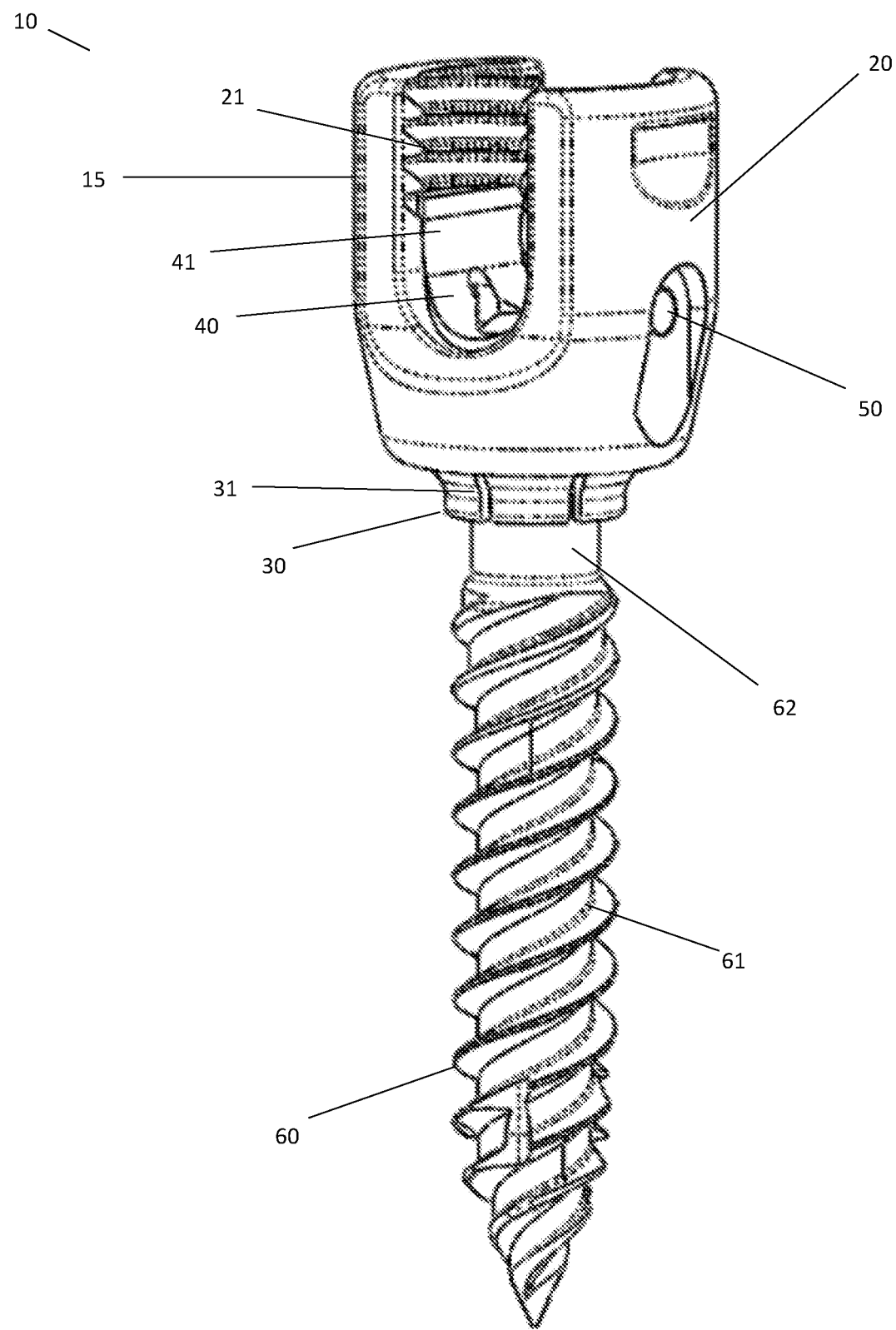
FIG. 1. is a perspective view of a detachable polyaxial pedicle screw in accordance with a first embodiment of the present invention.
Figure 2:
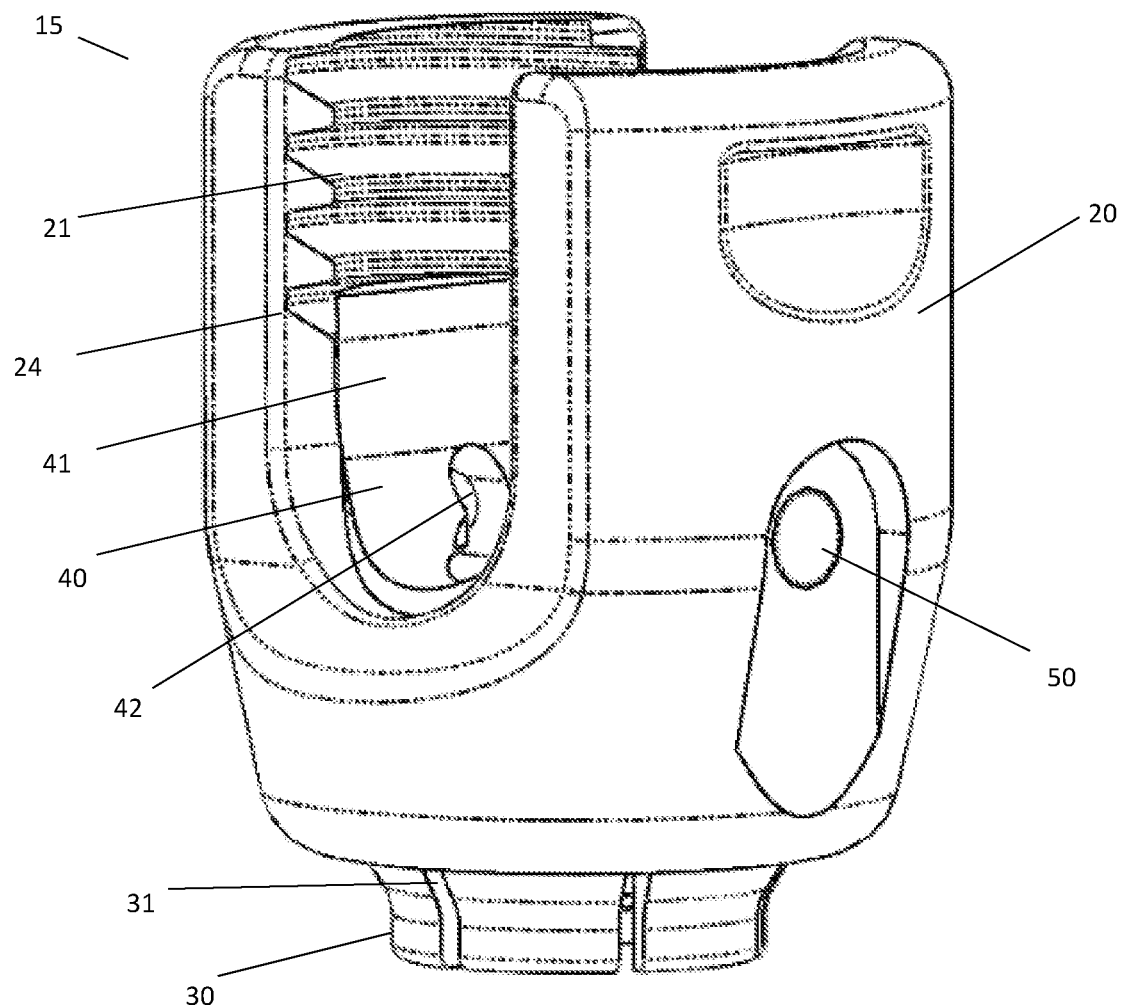
FIG. 2 is a perspective view of a detachable head of a detachable polyaxial pedicle screw in accordance with a first embodiment of the present invention.

In accordance with embodiments of the present invention, a detachable polyaxial pedicle screw device may comprise a bone screw and a detachable tulip head assembly comprising a tulip head, a locking member, a collet, and one or more connection members (e.g., one or more pins). In some embodiments, the locking member may be substantially globular or spherical and may be substantially hollow. In any embodiment, the connection members may be pins, screws, or any other similarly suitable connection members or fasteners which are capable of fastening two pedicle screw components, for example, a collet to a tulip head.

In accordance with embodiments of the present invention, a polyaxial pedicle screw locking member may comprise a substantially spherical body member formed with an aperture at a bottom portion of the spherical body member, an internal threaded portion, one or more central openings, one or more grooves (e.g., cuts, slots, or spaces), one or more locking tab members, one or more angled faces, one or more perpendicular faces, and a drive feature. In any embodiment, the spherical locking member may comprise more or fewer components, depending on the intended use for the spherical locking ball and/or the polyaxial pedicle screw device. In some examples, a portion of the spherical locking member, for example, a bottom portion of the spherical locking member may be formed with one or more grooves configured as cuts or slots in the bottom portion of the spherical locking member to form one or more locking tab elements in the bottom portion of the spherical locking member, for example, to collectively form an expandable aperture at a bottom portion of the locking member. The grooves and the central openings of the spherical locking member may be configured to enable and/or support the expansion of the spherical locking member, for example, by enabling the tab members to move or travel axially outward with respect to a central axis of the locking member. In some examples, some or all of the locking tab members may comprise internal threaded portions. In some embodiments, the internal threaded portion of the tab member may be configured to engage or mate with a head or top portion (e.g., a proximal portion) of a bone screw, for example, a threaded portion disposed on a top portion of a bone screw. In some scenarios, the locking member may be referred to herein as a locking ball.

In accordance with embodiments of the present invention, a pedicle screw device may comprise a bone screw member having a threaded head portion and a head assembly comprising a tulip member formed with a locking member aperture, a locking member disposed in the tulip member and comprising a top portion with a drive feature and a bottom portion formed with an expandable aperture having internal threads configured to threadably engage with the head portion of the bone screw, the locking member configured to enable polyaxial movement of the tulip member about the locking member before the tulip member is fixed in a user selected position relative to the bone screw, a collet member formed with an opening providing access to the locking member drive feature and one or more connectors connecting the tulip member to the collet member to prevent rotation of the collet member within the tulip member. In some embodiments, the locking member may be substantially globular. In some embodiments, the collet member may have a substantially flat bottom portion adapted to abut a top face of the locking member. In some embodiments, the expandable aperture may comprise one or more grooves disposed between two or more locking tabs, each locking tab comprising at least one face configured to engage with a portion of the bone screw member to prevent the locking member from counter-rotating with respect to the bone screw member. In some embodiments, the at least one face of the locking member locking tabs may abut a portion of one or more protruding tabs extending from the bone screw member to prevent counter-rotation of the locking member with respect to the bone screw member. In some embodiments, a set screw may secure a rod element to the head assembly and may compress the collet member towards the locking ball to direct the locking ball towards a base portion of the tulip member to lock the head assembly in a fixed position relative to the bone screw member.

In accordance with embodiments of the present invention, a pedicle screw device, may comprise a bone screw member having a head portion with one or more threads and a head assembly comprising a tulip member having an internal thread portion and a base portion comprising a locking member socket formed with a locking member aperture, a substantially globular locking member disposed in the locking member socket and comprising a top portion having a drive feature and a bottom portion disposed in the locking member aperture and formed with an expandable aperture having internal threads configured to engage with the head portion threads of the bone screw member, the locking member configured to enable swiveling of the tulip member about the locking member before the tulip member is fixed in a user selected position relative to the bone screw, a collet member having a substantially flat bottom portion adapted to abut the top portion of the locking member and formed with an opening enabling access to the locking member drive feature, and one or more connectors connecting the tulip member to the collet member to prevent rotation of the collet member within the tulip member. In some embodiments, a driver may be introduced through the collet member and into the drive feature of the locking member to threadably engage the locking member with the head portion of the bone screw. In some embodiments, a neck portion of the bone screw member may comprise one or more protruding tabs. In some embodiments, the expandable aperture of the locking member may comprise one or more locking tabs and one or more grooves configured to enable expansion of the expandable aperture. In some embodiments, one or more side walls of the locking member locking tabs may engage with the bone screw member protruding tabs to prevent counter-rotation of the locking member about the bone screw member. In some embodiments, a set screw may threadably engage with the internal thread portion of the tulip member to compress the collet member towards the locking ball to direct the locking ball towards the base portion of the tulip member to lock the head assembly.

In accordance with embodiments of the present invention, a pedicle screw tulip head assembly may comprise a tulip member having an internal thread portion, a base portion formed with a locking member aperture, a locking member socket, and one or more connector receiving holes, a locking member substantially corresponding in shape to the locking member socket of the tulip member and comprising top portion with a drive feature and a bottom portion with an expandable aperture, a collet member formed with an opening enabling access to the locking member drive feature and one or more connector slots, and one or more connectors insertable into the connector receiving holes of the tulip member and the connector slots of the collet member to connect the tulip member to the collet member to prevent rotation of the collet member within the tulip member. In some embodiments, the expandable aperture may comprise one or more grooves disposed between two or more locking tabs, each locking tab comprising at least one face configured to engage with a portion of a bone screw member to prevent the locking member from counter-rotating with respect to the bone screw member. In some embodiments, the at least one face of the locking member locking tabs may abut a portion of one or more protruding tabs extending from the bone screw member to prevent counter-rotation of the locking member with respect to the bone screw. In some embodiments, a set screw may secure a rod element to the head assembly and compress the collet member towards the locking ball to direct the locking ball towards a base portion of the tulip member to lock the head assembly in a fixed position relative to the bone screw member. In some embodiments, a set screw may threadably engage with the internal thread portion of the tulip member and compresses the collet member towards the locking ball to direct the locking ball towards the base portion of the tulip member to lock the head assembly in a fixed position relative to the bone screw member. In some examples, an exterior side wall of the tulip member of the head assembly may be connected to a rod retaining assembly comprising a tulip component and a collet component configured to retain a rod element. In some embodiments, the locking member may secure the tulip head assembly to a bone screw and a set screw may threadably engage with one or more internal threads of the rod retaining assembly tulip component to secure a rod in a rod aperture of the collet component.

Turning now to the figures, generally shown in FIGS. 1-12 is a detachable polyaxial pedicle screw device in accordance with a first embodiment of the present invention. As shown in the FIG. 1-3, a detachable polyaxial pedicle screw device 10 may comprise a detachable head assembly 15 and a bone screw member 60. The detachable head assembly 15 may comprise a tulip member 20 (e.g., a tulip head), a locking member 30, a collet member 40, and one or more connection members, for example, pins 50. As shown in the depicted example, the locking ball 30 may fit within (e.g., sit within) a tulip head 20, and may be retained by a collet 40. For example, at least a portion of the locking ball 30 may be sandwiched between the collet 40 and an internal base portion 28 of the tulip head 20, for example, in a socket or spherical cavity 23 of the tulip head 20. In some examples, the collet 40 may comprise one or more external threads adapted to engage with internal threads of the tulip head 20. The collet 40 may be retained within the tulip head 20 with one or more pins 50 and the locking ball 30 may be rotatable polyaxially within the tulip head 20. In some scenarios, the locking ball 30 may be rotatable polyaxially within the tulip head 20, relative to the aperture at a bottom portion of the tulip head 20.

Figure 3:
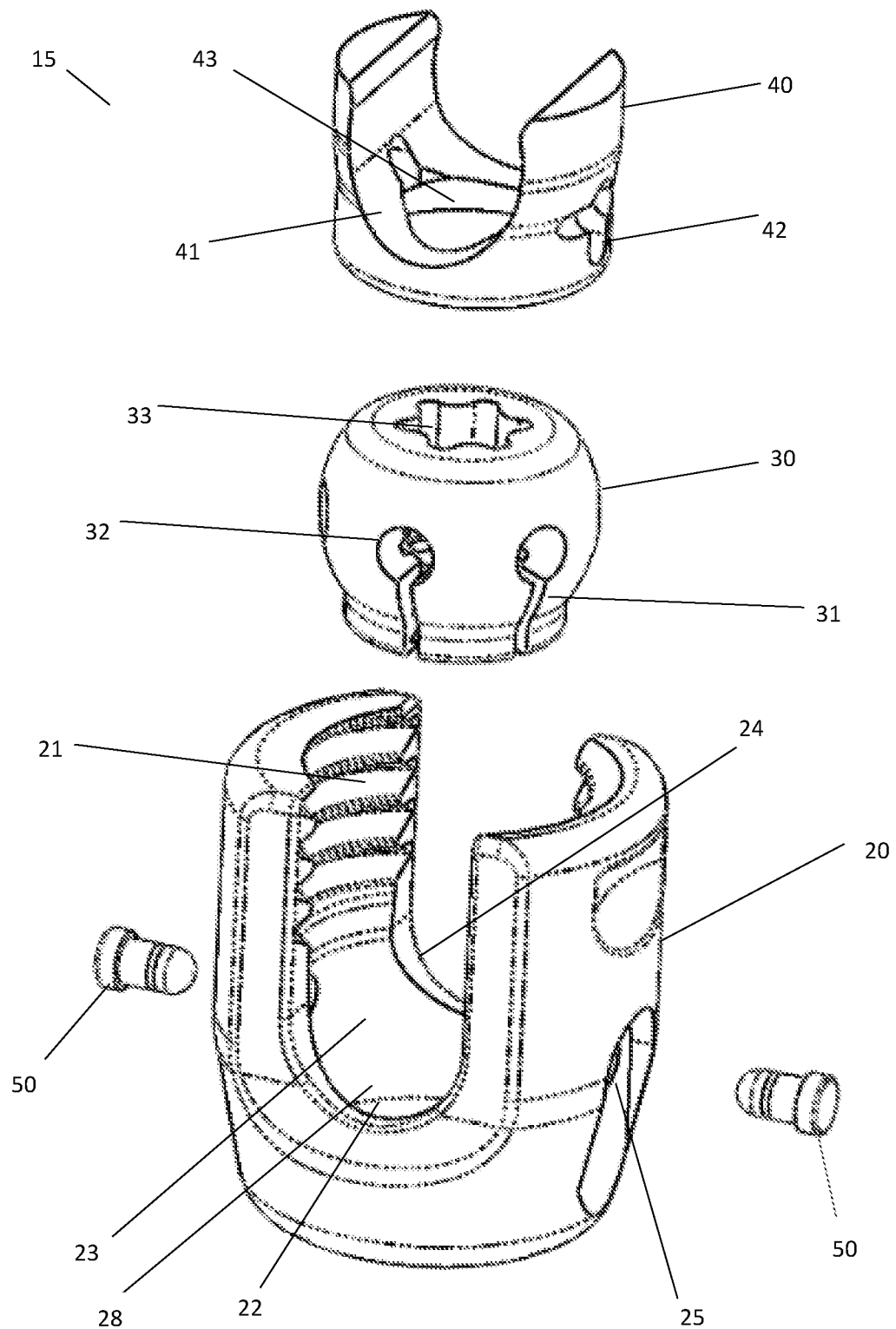
FIG. 3 is an exploded view of a detachable head of a detachable polyaxial pedicle screw in accordance with a first embodiment of the present invention.

As shown in FIG. 3, the locking ball 30 may be substantially spherical or globular and may substantially correspond in shape to a spherical or globular cavity 23 formed in the tulip head 20. In some examples, a bottom or distal portion of the locking ball 30 may protrude through an aperture 22 at a bottom portion of the tulip head 20. As shown in the depicted example, the collet 40 may be retained within the tulip head 20 by one or more pins 50 which may be configured to mate into one or more pin slots 42 of the collet 40 through one or more pin holes 25 of the tulip head 20. In some scenarios, this configuration may permit the collet 40 to slide or rotate axially within the tulip head 20. Likewise, the locking ball 30 may also slide or rotate axially within the tulip head 20, for example, in addition to the polyaxial rotation.

Figure 4:
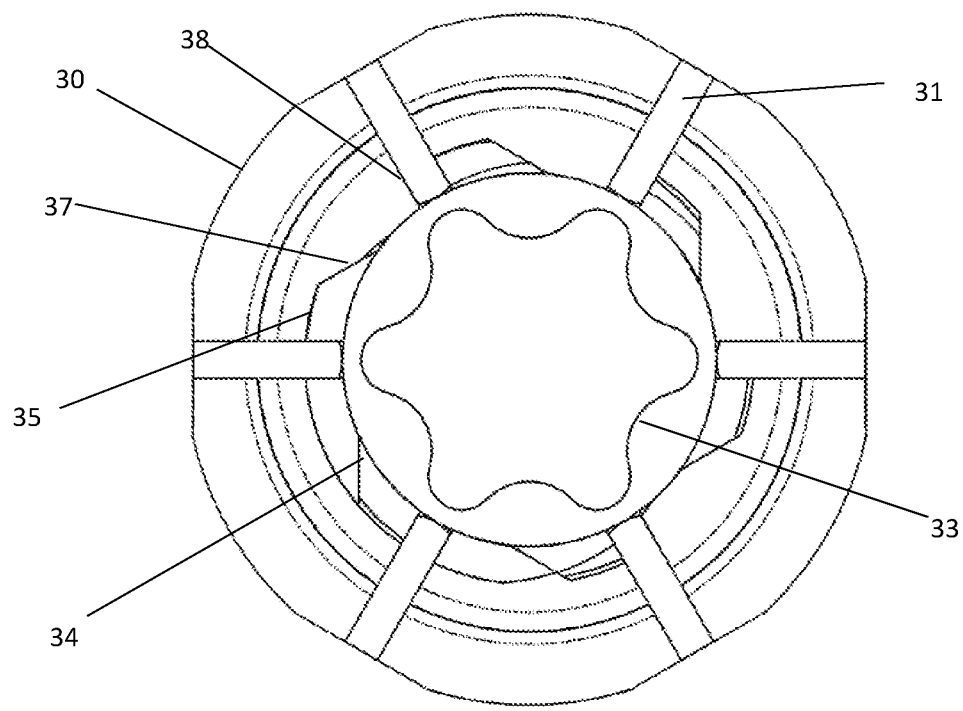
FIG. 4 is a bottom view of a locking ball of a detachable polyaxial pedicle screw in accordance with a first embodiment of the present invention.
Figure 5:
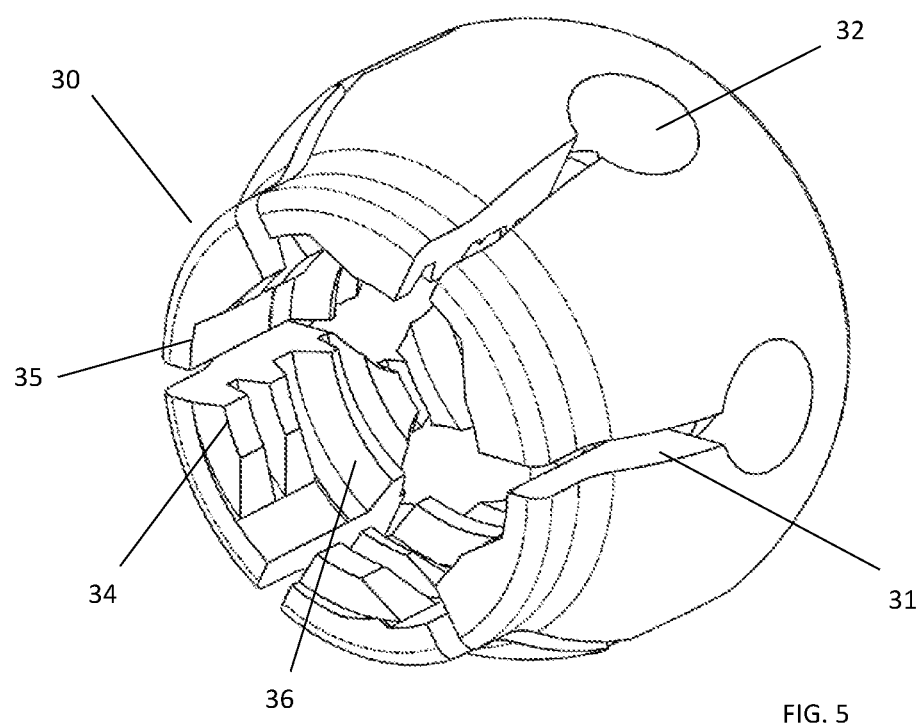
FIG. 5 is a perspective view of a bottom portion of locking ball of a detachable polyaxial pedicle screw in accordance with a first embodiment of the present invention.

As shown in FIGS. 3-5, the locking ball 30 may have grooves 31 and central openings 32 which may allow an aperture 34 at a bottom portion of the locking ball 30 to expand, for example, by enabling the locking tab members 35 to move or travel axially outward with respect to a central axis of the locking member 30. For example, when the locking ball 30 is allowed to move upwards (e.g., proximally) in the tulip head 20, for example, prior to the locking of the assembly 15 with a rod element 70 and set screw 80, the combination of the locking tabs 35 and the grooves 31 (and optionally including central cuts 32) may enable the aperture 34 at the bottom portion of the locking ball to expand within the aperture 22 at a bottom portion of the tulip head 20. For example, the size of the grooves 31 may expand or grow, in some scenarios, enabled by the central cuts 32, to increase the distance between respective locking tab members 35 and expand the aperture 34 of the locking member 30. In some scenarios, as the locking ball 30 is pressed downward (e.g., distally) within the tulip head's 20 spherical cavity 23 and towards the aperture 22 at a bottom portion of the tulip 20, for example, when a rod element 70 is placed in the collet 40 of the tulip head assembly 15 and a set screw 80 mates with the internal threads of the tulip head 20 to lock the rod element 70 and the rest of the tulip head assembly in place, the aperture 34 at the bottom portion of the locking ball 30 may be locked into place (e.g., no longer expand).

In some scenarios, in addition to the one or more pins 50 retaining the collet 40 within the tulip head 20, the pins 50 may also prevent the collet 40 from rotating within the tulip head 20, for example, to support alignment and/or securement of the rod aperture 41 of the collet 40 with the rod aperture 24 of the tulip head 20. In some examples, the rod aperture 41 of the collet 40 and the rod aperture 24 of the tulip head 20 may be substantially u-shaped. In any embodiment, the rod apertures 41 and/or rod apertures 24 may be formed in any similarly shape to enable a rod element 70 to engage with the collet 40 or tulip 20, for example, the rod apertures 41 and/or 24 may substantially correspond in shape to an exterior profile of a rod element 70 to sufficiently engage and/or retain a given rod element 70. In some embodiments, a central aperture 43 of the collet 40 may permit a driver (not shown) to go through the central aperture 43 of the collet 40 and engage with a drive feature 33 disposed on a top or proximal portion of the locking ball 30.

Figure 6:
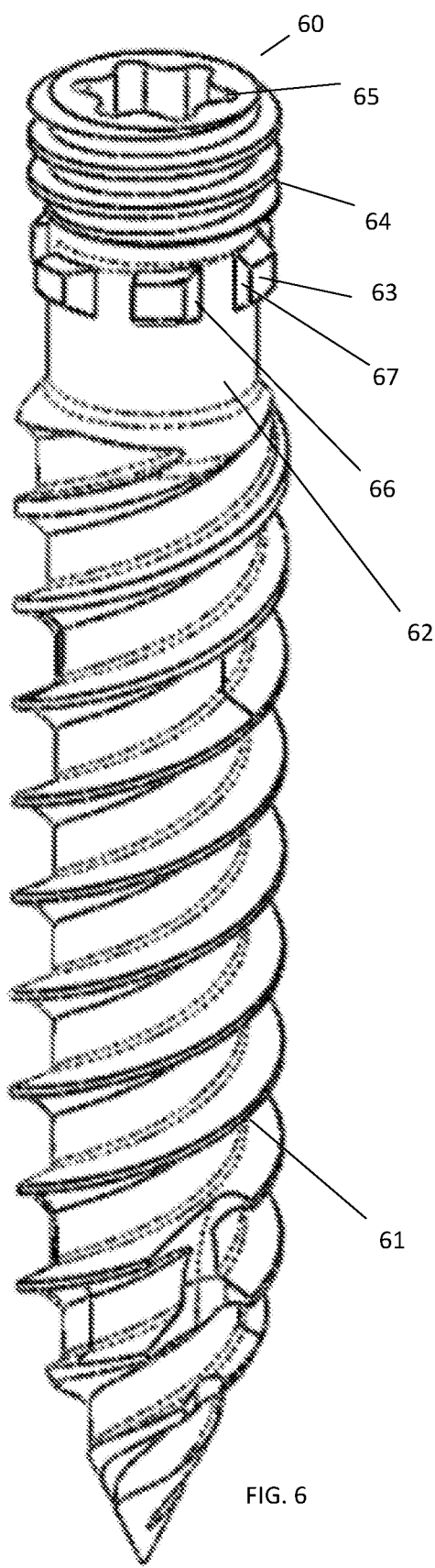
FIG. 6 is a perspective view of a bone screw of a detachable polyaxial pedicle screw in accordance with a first embodiment of the present invention.

As shown in FIG. 4, a bottom side (e.g., a bottom portion) of the locking ball 30 may comprise an aperture 34 which may be formed to receive a bone screw 60 (shown in FIG. 6). The bottom portion of the locking ball 30 may comprise one or more locking tabs 35, which may be distanced from one another by one or more grooves 31 and/or one or more central openings 32. In some embodiments, the locking tabs 35 may have one or more angled faces 37 and one or more perpendicular faces 38. An angled face 37 of the locking tab 35 may be angled with respect to the radius of the locking ball 30, and a perpendicular face 38 may be perpendicular to a counter clockwise rotation of the locking ball 30. Internal threads 36 may be disposed between the locking tabs 35 and the drive feature 33 on the locking ball 30. The internal threads 36 may also be formed on an internal portion of the locking tabs 35.

Figure 7:
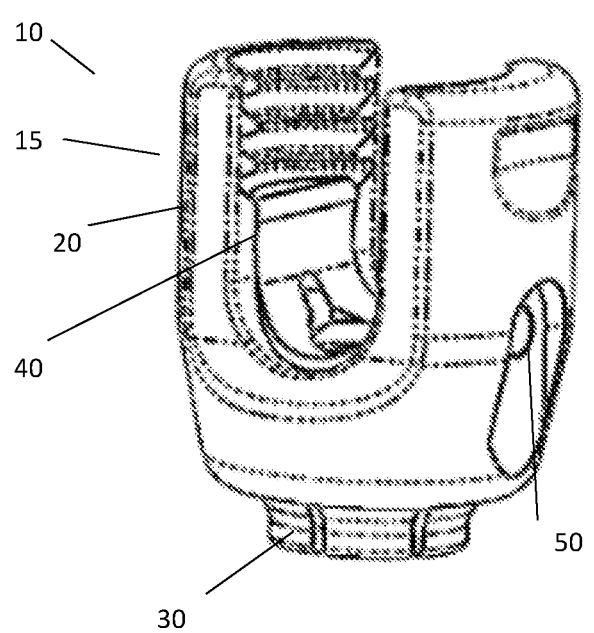
FIG. 7 is an exploded perspective view of a detachable polyaxial pedicle screw in accordance with a first embodiment of the present invention.
Figure 7:
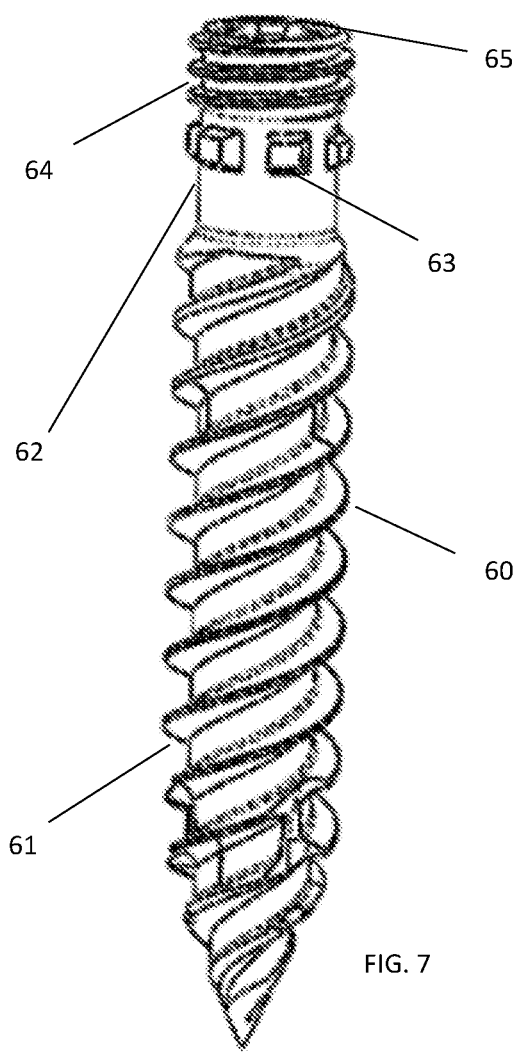

As shown in FIGS. 6-7, a bone screw 60 may comprise bone threads 61 on a bottom (e.g. distal) portion of the bone screw 60 which may be configured (e.g., formed) to engage with a vertebral body, for example, vertebrae V1, V2. In some examples, above the bone threads 61 may be a head and/or a neck portion 62 of the bone screw 60. A top face of the bone screw 60 may comprise a drive feature 65. Head portion threads 64 may extend axially from the top portion of the bone screw 60. In some examples, a top portion of the bone screw 60 may comprise one or more protruding or locking tabs 63. For example, one or more protruding or locking tabs 63 may be located on the neck portion 62 of the bone screw 60, for example, between the head portion threads 64 and the bone threads 61. In some examples, the locking tabs 63 may extend or protrude axially from the neck portion 62 of the bone screw 60. The locking tabs 63 may have one or more angled faces 66, which may be angled with respect to the radius of the neck portion 62 of the bone screw 60. Additionally, in some embodiments, the one or more locking tabs 63 of the bone screw 60 may have one or more perpendicular faces 67, which may be perpendicular to a counter clockwise rotation of the head portion threads 64.

Figure 8:
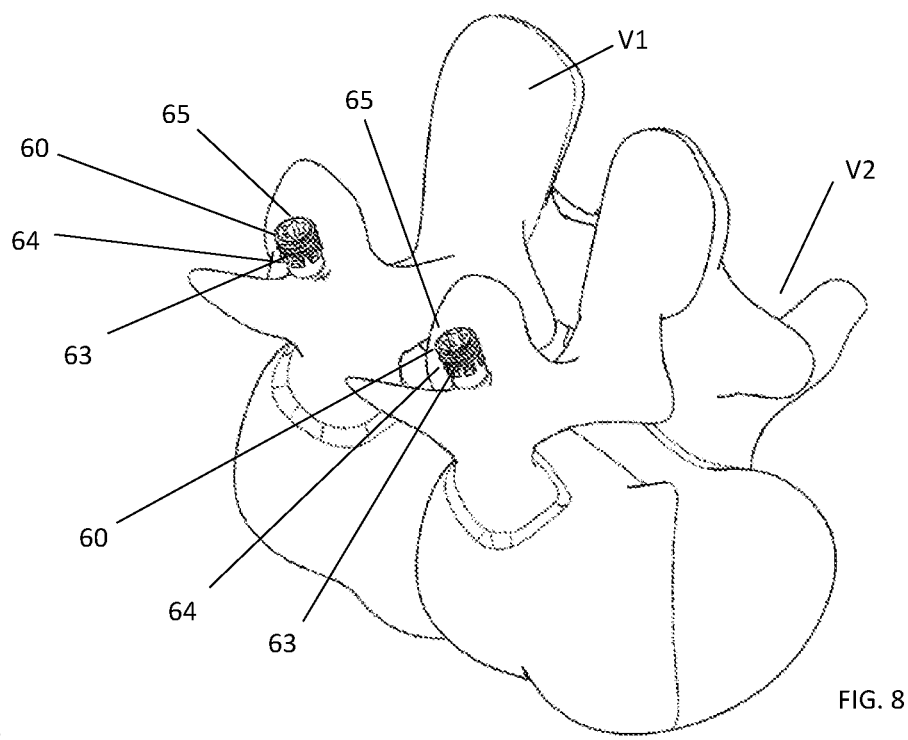
FIG. 8 is a perspective view of bone screws of a detachable polyaxial pedicle screw in an exemplary spine in accordance with a first embodiment of the present invention.
Figure 9:
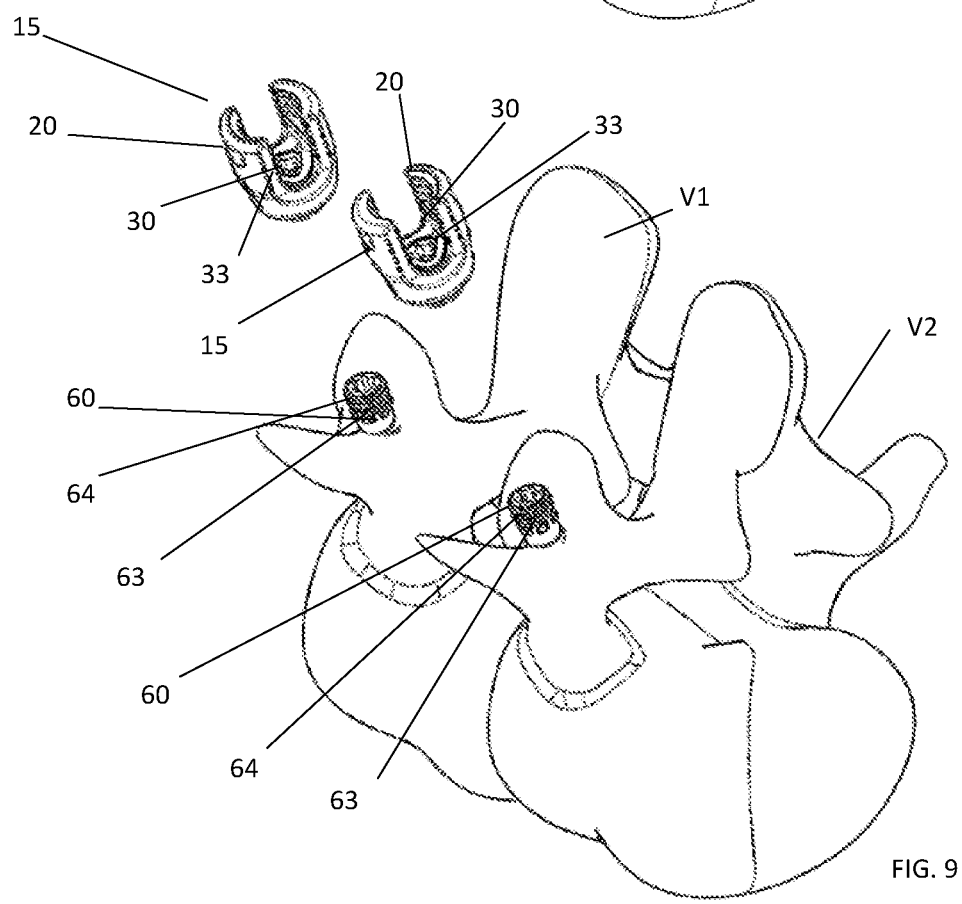
FIG. 9 is a perspective view of an exemplary usage scenario wherein detachable heads are positioned to be lowered onto bone screws of a detachable polyaxial pedicle screw attached to a spine in accordance with a first embodiment of the present invention.

FIG. 8 depicts an illustrative example of bone screws 60 set in a spine. As shown in FIG. 8, the bone screws 60 may be implanted into vertebral bodies, for example, vertebrae V1, V2, in a manner which leaves the neck portion 62, as well as the one or more protruding or locking tabs 63 and head portion threads 64 of each of the shown bone screws 60 exposed. As shown in FIG. 9, tulip head assemblies 15 may then be introduced with a driver (not shown) extending through the central aperture 43 of the collets 40 and into a drive feature 33 of each of the locking balls 30. A threaded portion of the locking balls 30, for example, internal threads 36 of each locking ball 30 may then be threaded onto the head portion threads 64 of the bone screw 60. Each of the locking balls 30 may be allowed to recess within the tulip head 20, to support expansion of the aperture 34 at the bottom portion of the locking balls 30. In some scenarios, this configuration may permit or support the angled faces 37 of the locking ball 30 locking tabs 35 to come into contact with the angled faces 66 of the bone screw 60 locking tabs 63. In accordance with embodiments of the present invention, the locking ball may configured to act as a joint about which the socket or spherical cavity 23 of the tulip 20 may pivot, rotate or swivel.

In an illustrative example, as the locking ball 30 is threaded onto the bone screw 60, the angled faces 37 of the locking ball 30 and the angled faces 66 of the bone screw 60 may force the aperture 34 at the bottom portion of the locking ball 30 to expand to permit the locking tabs 35 of the locking ball 30 and the locking tabs 63 of the bone screw 60 to move past one another, allowing the locking ball 30 to continue to be threaded down. However, the perpendicular faces 38 of the locking ball 30 and the perpendicular faces 67 of the bone screw may prevent the locking ball 30 from rotating counter-clockwise to prevent the locking ball 30 from unthreading with regards to (e.g., disconnecting or disassembling from) the bone screw 60.

Figure 10:
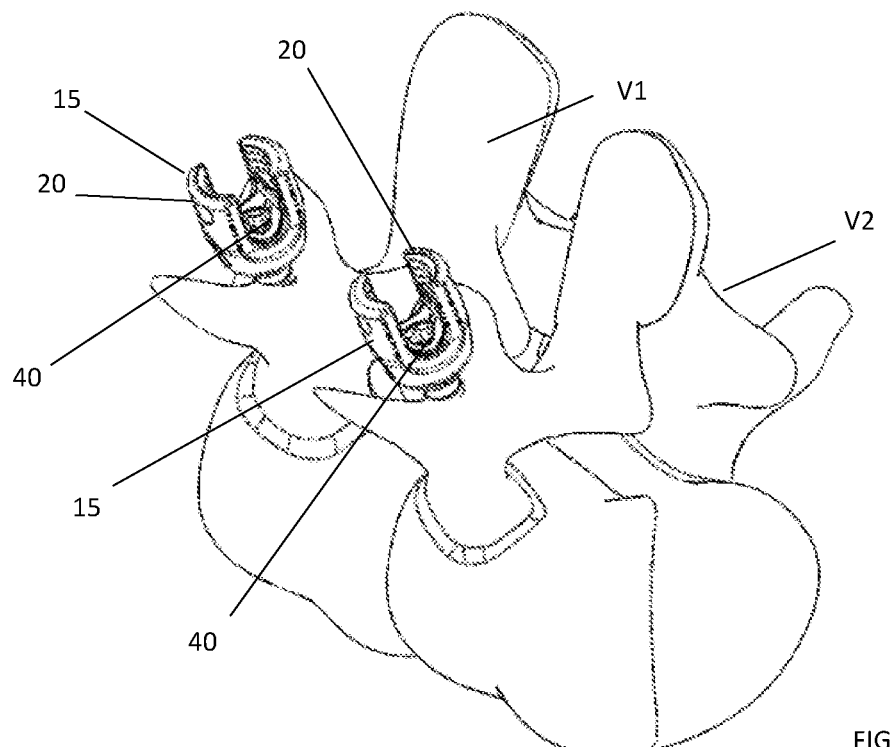
FIG. 10 is a perspective view of bone screws set in a spine and attached to detachable heads of detachable polyaxial pedicle screws in accordance with a first embodiment of the present invention.
Figure 11:
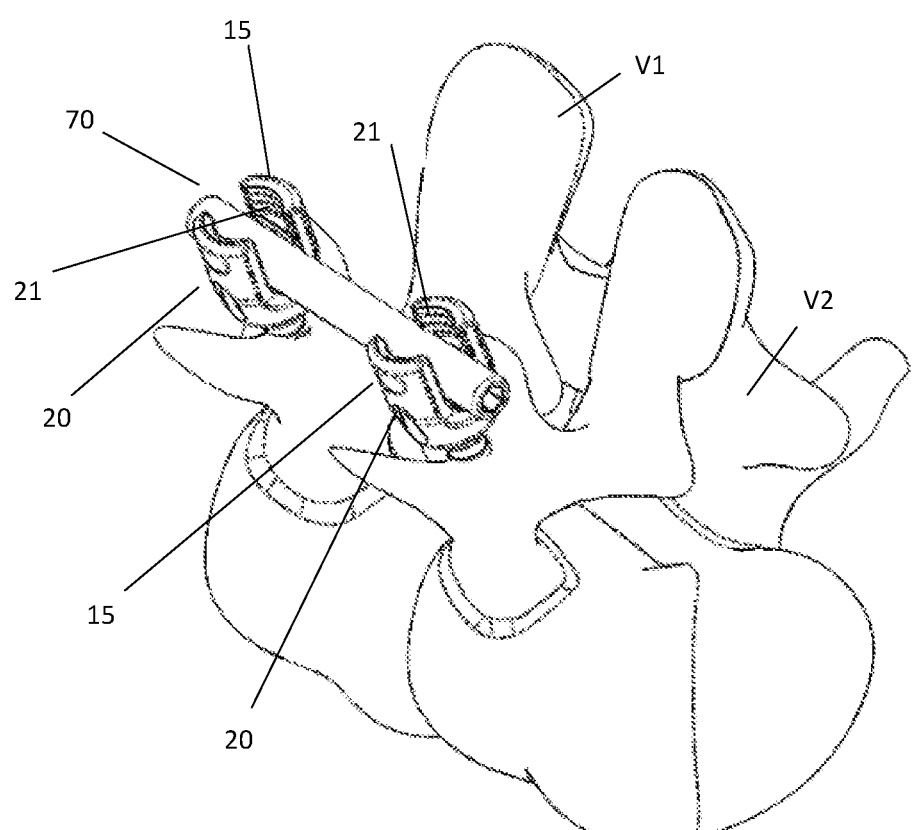
FIG. 11 is a perspective view of a rod connecting detachable heads of a pair of detachable polyaxial pedicle screws set in a spine in accordance with a first embodiment of the present invention.
Figure 12:
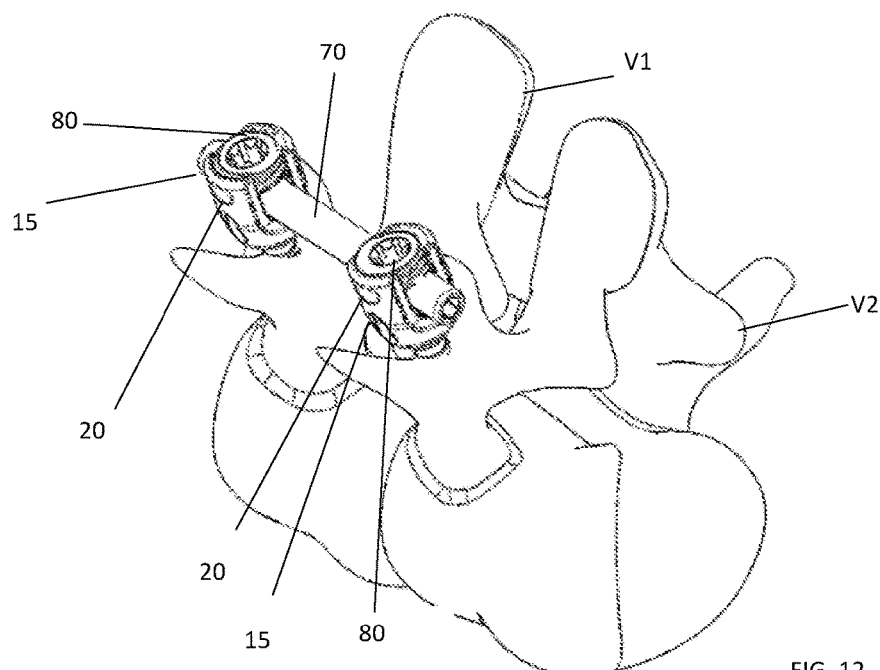
FIG. 12 is a perspective view of set screws locking a rod connecting detachable heads of a detachable polyaxial pedicle screw in accordance with a first embodiment of the present invention.

As shown in FIG. 10, in some scenarios, once the locking ball 30 is in place on the bone screw 60, the detachable polyaxial pedicle screw device 10 may be configured to act like a typical polyaxial screw, where the tulip head 20 may rotate or swivel about the locking ball 30, before the position of the head assembly 15 is fixed relative to the bone screw 60. In an exemplary usage scenario, for example, as shown in FIGS. 11-12, a rod element 70 may be introduced into one or more rod apertures 41 of the collet members 40 to form a connection between adjacent devices 10. The rod element 70 may be any linear or non-linear implement which is suitable for connecting a pair of head assemblies 15. Subsequently, in some examples, a set screw 80 may be threaded into the locking threads 21 of the tulip head 20. The set screw 80 may force the rod element 70 down into the collet 40, to compress the collet 40 around the rod element 70 and lock and/or secure it into place. This action may also force the collet 40 towards and/or onto the locking ball 30 (e.g., may compress the collet 40 and the locking ball 30), and force the locking ball 30 towards a base portion 28 of the spherical cavity 23 of the tulip head 20, to lock the assembly in a desired position (e.g., a chosen position for the tulip head relative to the bone screw, for example, the tilt or angle of the tulip head relative to the bone screw).

In accordance with embodiments of the present invention, threading the set screws 80 into the locking threads 21 of the tulip head 20 may lead the locking ball 30 aperture 34 at a bottom portion of the locking ball 30 to compress, to support (e.g., ensure) engagement of the locking tabs 35 of the locking ball 30 and locking tabs 63 of the bone screw 60, for example, such that the locking ball 30 cannot counter rotate on the (e.g., with respect to) the bone screw 60. In another illustrative example, threading the set screws 80 into the locking threads 21 of the tulip head 20 may direct the locking tabs 35 of the locking ball 30 to a position between the locking tabs 63 of the bone screw 60, for example, such that the perpendicular faces 67 of the bone screw 60 and the perpendicular faces 38 of the locking ball 30 substantially abut each other to prevent counter-rotation of the locking ball 30 with respect to the bone screw 60. Additionally, threading the set screws 80 into the locking threads 21 of the tulip head 20 may create a friction weld between the locking ball 30 and tulip head 20 to prevent any further motion between the two components. In accordance with embodiments of the present invention, this configuration may create a rigid construct which substantially prevents disassembly of the device 10 in situ.

Figure 13:
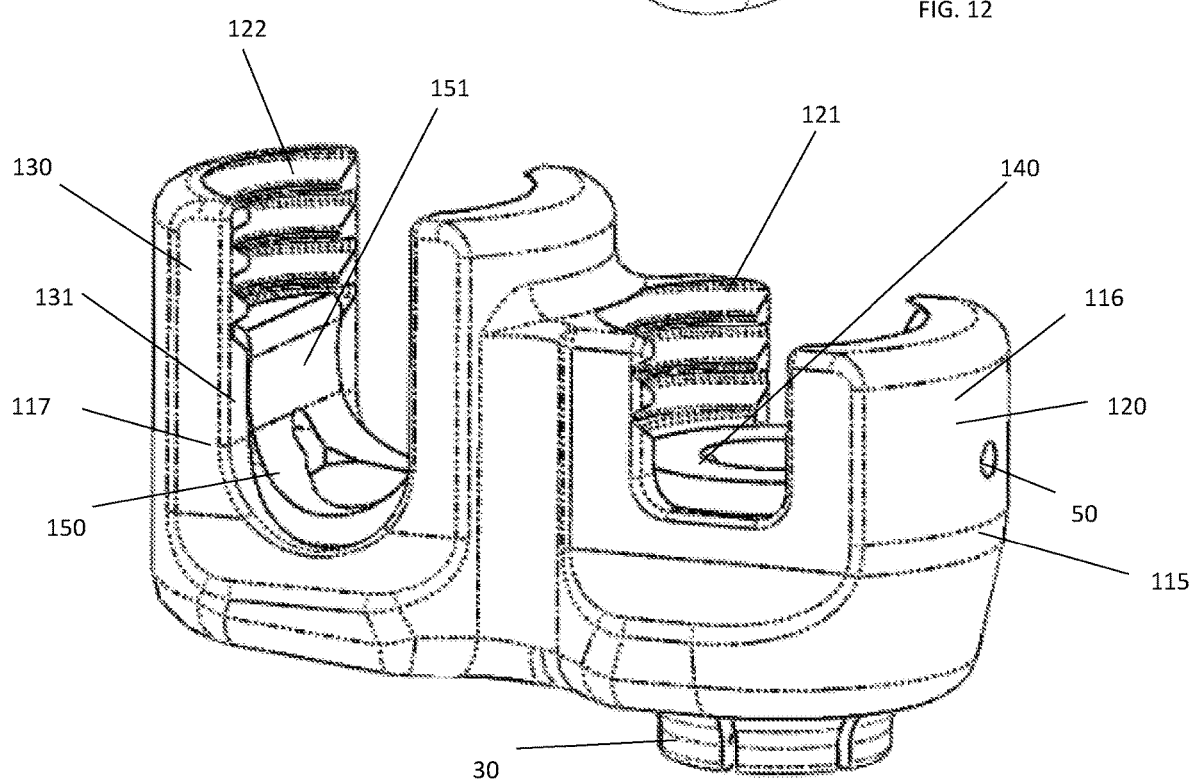
FIG. 13 is a perspective view of a detachable head of a detachable polyaxial pedicle screw in accordance with a second embodiment of the present invention.
Figure 14:
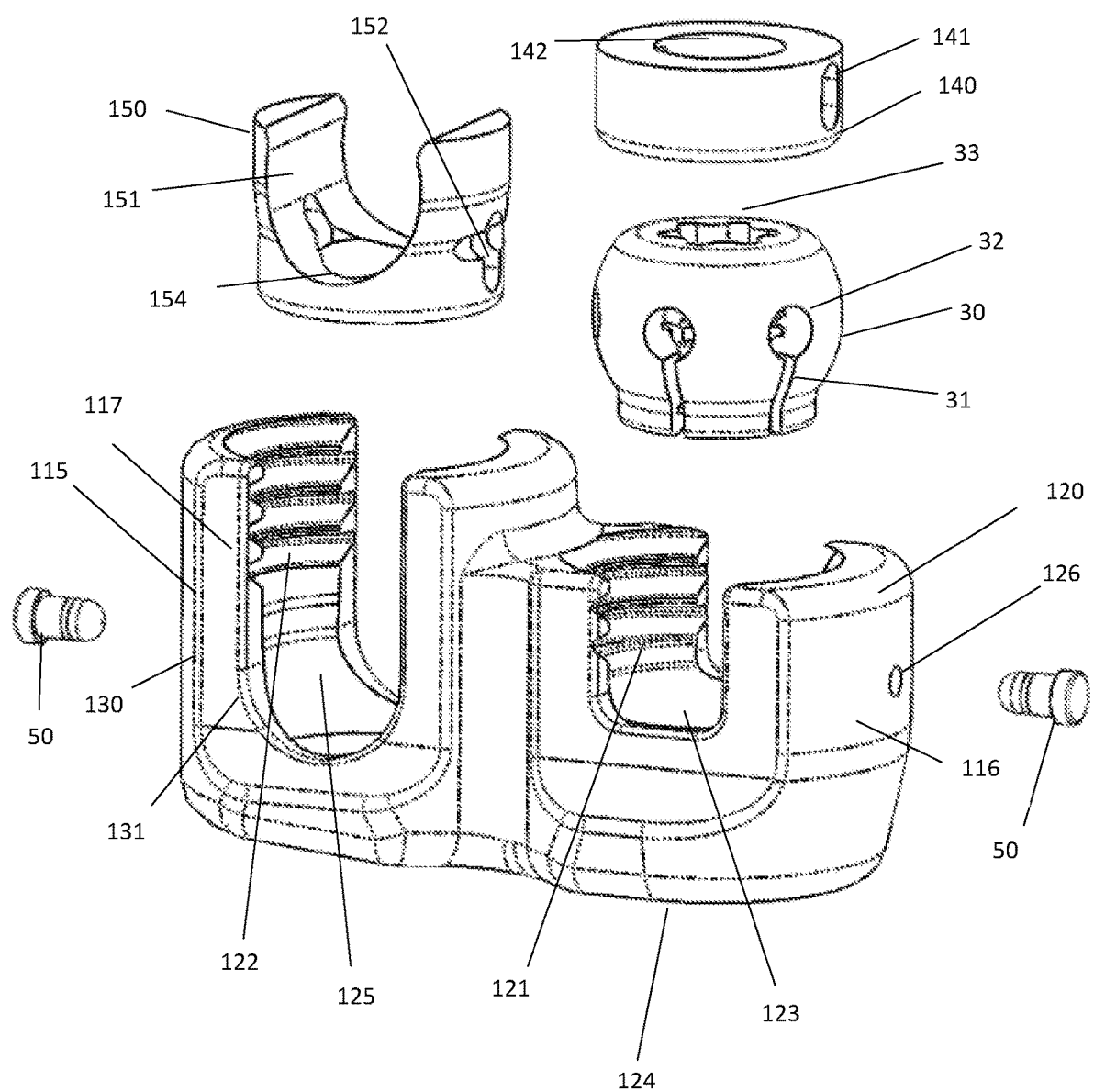
FIG. 14 is an exploded perspective view of a detachable polyaxial pedicle screw in accordance with a second embodiment of the present invention.
Figure 15:
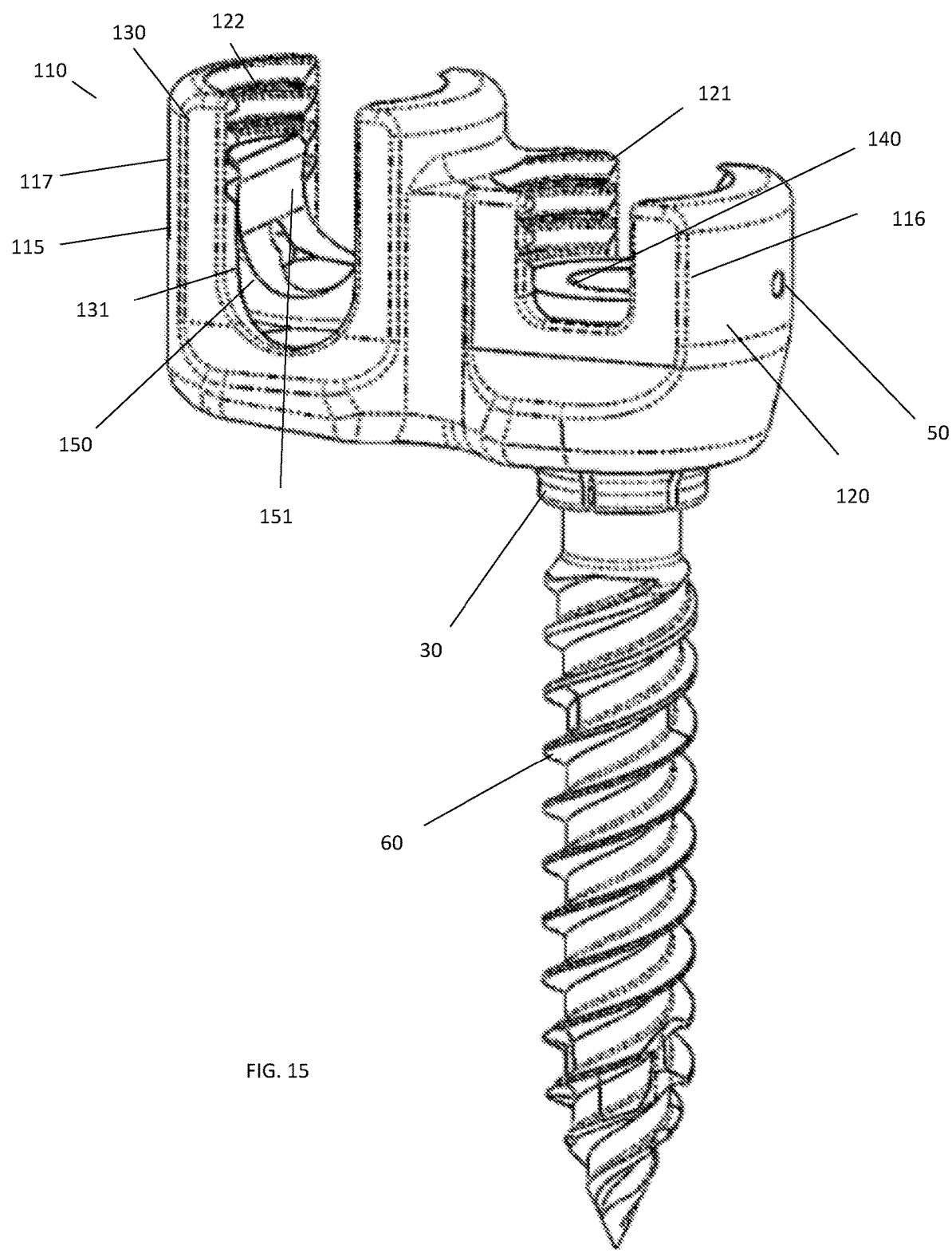
FIG. 15 is a perspective view of a detachable polyaxial pedicle screw in accordance with a second embodiment of the present invention.

FIGS. 13-16 generally depict a detachable polyaxial pedicle screw device 110 in accordance with a second embodiment of the present invention. As shown in the figures, a detachable polyaxial pedical screw may comprise a dual head assembly 115 and a bone screw 60. The dual head assembly 115 may comprise a dual tulip head (e.g., a first tulip head or member 120 and a second tulip head or member 130), a locking ball 30, a ball collet 140, a rod collet 150, and one or more connection members, for example, pins 50. In some examples, the dual tulip head may comprise a first tulip head assembly 116 and a second tulip head assembly 117. In some examples, the first tulip head assembly 116 may be to secure to a bone screw 60, and the second tulip head assembly 117 may be configured to retain or secure a rod element 70. In some examples, the first tulip head assembly 116 may be connected at an exterior side wall of the tulip head assembly 116 to a second tulip head assembly 117. In some examples, a first tulip head assembly 116 may comprise a first tulip member 120, a locking ball 30 and a collet member 140. The tulip member 120 may be configured with internal threads adapted to engage with a set screw 80. In some examples, a second tulip head assembly 117 may comprise a second tulip member 130, a locking ball 30 and a collet member 150. In some embodiments, the locking member 30 may secure the first tulip head assembly 116 to a bone screw 60 and a first set screw 80 may threadably engage with one or more internal threads of the first tulip member 120 go compress the collet 140 towards the locking member 30 to secure the first tulip head assembly 116 to the bone screw 60, and a second set screw 80 may threadably engage with one or more internal threads of the second tulip member 130 of the second tulip head assembly 117 to secure a rod element 70 in a rod aperture 151 of the collet member 150 and a rod aperture 131 of the tulip head 130. The rod aperture 151 of the collet member 150 and the rod aperture of the tulip head 130 may be substantially u-shaped or any other similarly suitable shape adapted to receive and/or retain a rod element 70. As shown in the depicted example, the locking ball 30 may fit within (e.g., sit within) a socket or spherical cavity 123 of the first tulip head assembly 116, and may be retained by a collet member 140 (e.g., a ball collet). As shown in FIGS. 13 and 14, in some embodiments, the collet member 140 may have substantially flat top and bottom sides and may be retained within the first tulip head assembly 116 with one or more pins 50. The collet member 140 may comprise an aperture 142 adapted to permit access to the locking ball drive feature 33. In some embodiments, the locking ball 30 may rotate polyaxially within the socket or spherical cavity 123 of the first tulip head assembly 116. Additionally, a collet member 150 (e.g., a rod collet) may fit within (e.g., sit within) a cylindrical, spherical or globular cavity 125 of the second tulip head assembly 117. The rod collet 150 may similarly comprise an aperture 154 adapted to permit access to the locking ball drive feature 33 and may likewise be retained within the dual head assembly 115 with one or more pins 50.

The spherical locking ball 30 may fit (e.g., sit in) a spherical cavity 123 of the first tulip head assembly 116 and protrude through an aperture 124 at a bottom portion of the first tulip head assembly 116. The ball collet 140 which may be retained within the dual head assembly 115 by one or more pins 50 which may mate into one or more pin slots 141 of the ball collet 140 through one or more pin holes 126 of the dual head assembly 115. This may permit the ball collet 140 to slide axially within the dual head assembly 115, for example, within the first tulip head 120 of the dual head assembly 115. Likewise, the locking ball 30 may also slide axially within the first. Tulip head 120, in addition to polyaxial rotation. The central aperture 142 of the ball collet 140 may allow for a driver (not shown) to go through the ball collet 140 and engage with a drive feature 33 of the locking ball 30.

Similarly, the one or more pins 50, which may extend through the one or more pin holes 126 of the dual head assembly 115, for example, the second tulip head 130, and into one or more pin slots 152 of the rod collet 150, may allow the rod collet 150 to slide axially within a cylindrical aperture 125 of the dual tulip head 120. In some scenarios, in addition to the pins 50 retaining the rod collet 150 within the second tulip head. 130 of the dual tulip head assembly 115, the pins 50 may also prevent the rod collet 150 from rotating within the second tulip head 130 of the dual tulip head assembly 115. In some examples, this configuration supports alignment and/or securement of the rod aperture 151 of the rod collet 150 with a rod aperture 131 of the second tulip head 130.

In accordance with embodiments of the present invention, the locking ball 30 may comprise grooves 31 and central openings 32 which may allow an aperture 34 at a bottom portion of the locking ball to expand. When the locking ball 30 is allowed to move upwards (e.g., proximally) in the first tulip head 120, the aperture 34 of the locking ball can expand within the aperture 124 at the bottom portion of the first tulip head 120. However, as the locking ball 30 is pressed downward (e.g., distally) within the first tulip head's 120 spherical cavity 123 and aperture 124, the aperture 34 of the locking ball 30 may no longer expand.

Figure 16:
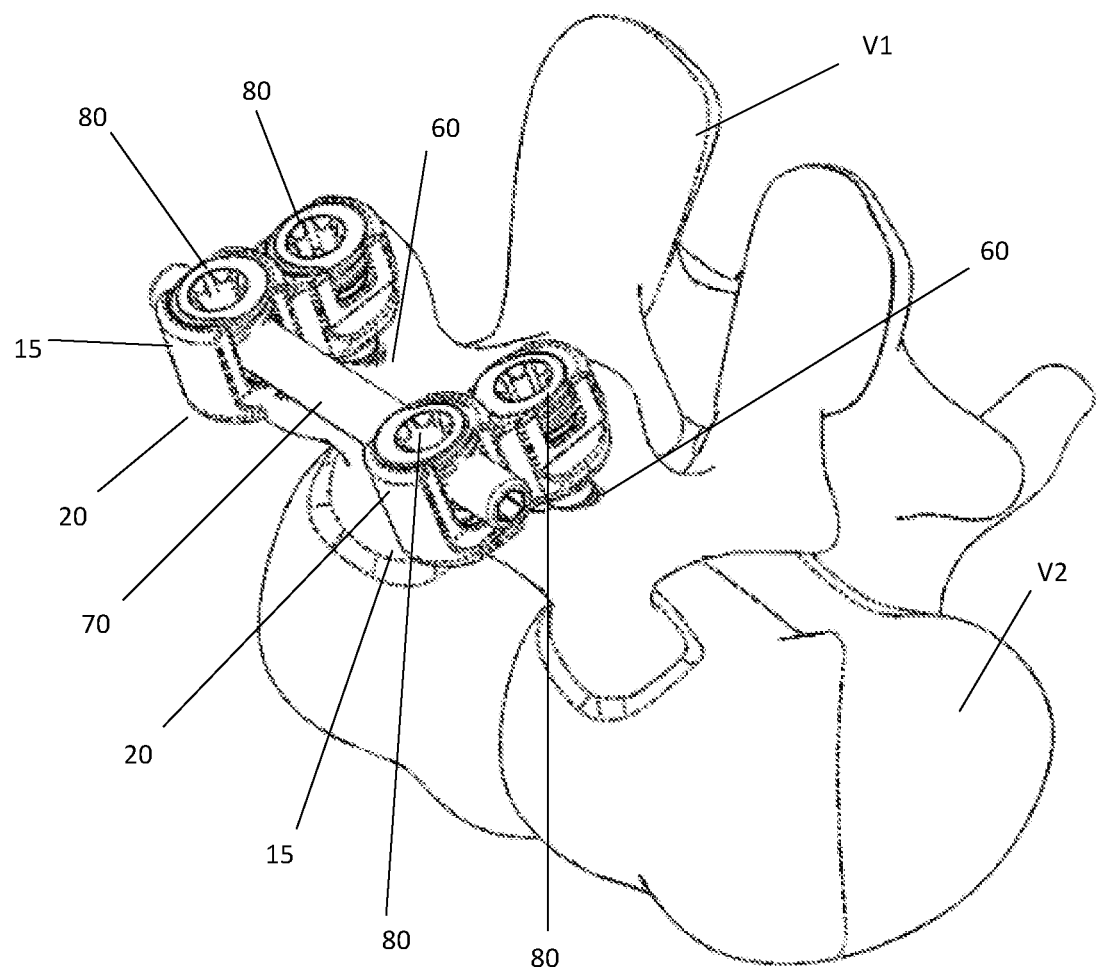
FIG. 16 is a perspective view of set screws locking a rod connecting a pair of detachable heads set in a spine in accordance with a second embodiment of the present invention.

FIG. 16 depicts an illustrative example of detachable dual head polyaxial screw devices set in a spine in accordance with embodiments of the present invention. As shown in the depicted example, one or more bone screws 60 may be implanted into a spine, for example, at vertebrae V1, V2. In some scenarios, the position of the bone screws 60 may be set within a spine, leaving the neck portion 62 of the bone screws, as well as the locking tabs 63 and head portion threads 64 of the bone screw(s) 60 exposed. A dual tulip head assembly 115 may then introduced with a driver (not shown) extending through an aperture 142 of the ball collet 140 and into the drive feature 33 of a locking ball 30. The internal threads 36 of the locking ball 30 may then be threaded onto the head portion threads 64 of a bone screw 60. The locking ball 30 may be permitted to recess within the first tulip head 120, for example, within the socket or spherical cavity 23 of the first tulip head 120, to allow an aperture 34 at a bottom portion of the locking ball 30 to expand. In some examples, one or more angled faces 37 of the locking ball 30 locking tabs 35 may come into contact with one or more angled faces 66 of the bone screw 60 locking tabs 63, and as the locking ball 30 is threaded down onto the bone screw 60, the angled faces 37 of the locking ball 30 and the angled faces of the bone screw 66 may force the aperture 34 at the bottom portion of the locking ball 30 to expand, allowing the locking tabs 35 of the locking ball 30 and the locking tabs 63 of the bone screw 60 to move past one another, to permit the locking ball 30 to continue to be threaded down. However, one or more perpendicular faces 38 of the locking ball 30 and the perpendicular faces 67 of the bone screw may prevent the locking ball 30 from rotating counterclockwise to prevent the locking ball 30 from unthreading with regards to (e.g., disconnecting or disassembling from) a bone screw 60.

As further shown in FIG. 16, in some scenarios, once the locking ball 30 is in place on a bone screw 60, the detachable dual head polyaxial screw device 110 may act like a typical polyaxial screw, where one or more dual tulip head assemblies 115 may rotate about the locking ball 30. In an exemplary usage scenario, for example, as shown in FIG. 16, a rod element 70 may be introduced into the rod apertures 151 of the rod collets 150 and the rod apertures 131 of the second tulip head 130 in order to connect to adjacent devices 110. Subsequently, in some scenarios, set screws 80 may be threaded into the locking threads 122 of the second tulip head 130. The set screws 80 may force the rod element 70 down into the rod collets 150, to compress the rod collets 150 around the rod element 70 and lock the rod element 70 into place. Similarly, set screws 80 may be threaded into the locking threads 121 of the first tulip head 120. In some embodiments, this action may also force the ball collet 140 onto the locking ball 30, and may force the locking ball 30 into the spherical cavity 123 in the base portion of the first tulip head 120. In some scenarios, this action may compress the locking ball 30 aperture 34 to support engagement and/or securement of the locking tabs 35 of the locking ball 30 and the locking tabs 63 of the bone screw 60 (e.g., such that the locking ball 30 is prevented from counter rotating on the bone screw 60). Additionally, in some examples, this action may form a friction weld between the locking ball 30 and dual tulip head assembly 115, for example, at the first tulip head 120, to substantially prevent motion between the two components (e.g., the locking member 30 and the dual tulip head assembly 115). In accordance with embodiments of the present invention, this configuration may create a rigid construct which cannot disassemble in situ.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments. elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most fastener %" means fastener % or less than fastener %. When, in this specification, a range is given as "(a first number) to (a second number)" or "(a first number)— (a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. A pedicle screw device, comprising:
   a bone screw member having a threaded head portion; and
   a head assembly comprising:
      a tulip member formed with a locking member aperture;
      a locking member comprising a top portion with a drive feature and a bottom portion formed with an expandable aperture having internal threads configured to threadably engage with the threaded head portion of the bone screw, wherein the locking member is disposed in the tulip member;
      a collet member formed with an opening providing access to the drive feature of the locking member; and
      one or more connectors connecting the tulip member to the collet member to prevent rotation of the collet member within the tulip member.

2. The pedicle screw device of claim 1, wherein the locking member is substantially globular.

3. The pedicle screw device of claim 1, wherein the collet member has a substantially flat bottom portion adapted to abut a top face of the locking member.

4. The pedicle screw device of claim 1, further comprising one or more locking tabs on the expandable aperture that are distanced from each other by a groove or opening, each locking tab having an inner surface comprising at least one face configured to engage with a portion of the bone screw member to prevent the locking member from counter-rotating with respect to the bone screw member.

5. The pedicle screw device of claim 4, further comprising a plurality of protruding tabs extending from a neck portion of the bone screw member that is between the threaded head portion and a threaded bone portion of the bone screw, wherein the at least one face of each locking tab is configured to engage with one or more of the protruding tabs to prevent counter-rotation of the locking member with respect to the bone screw member.

6. The pedicle screw device of claim 5, wherein the protruding tabs are spaced apart and aligned around a circumference of the neck portion of the bone screw.

7. A pedicle screw device, comprising:
   a bone screw member having threaded head portion, a plurality of protruding tabs, and a threaded bone portion, wherein the protruding tabs extend from a neck portion that is between the threaded head portion and the threaded bone portion; and
   a head assembly comprising:
      a tulip member having an internal thread portion and a base portion comprising a locking member socket formed with a locking member aperture;
      a locking member comprising a bottom portion disposed in the locking member aperture, wherein the locking member is formed with internal threads configured to engage with the threaded head portion threads of the bone screw member;
      a collet member having a substantially flat bottom portion adapted to abut the locking member; and
      one or more connectors connecting the tulip member to the collet member to prevent rotation of the collet member within the tulip member.

8. The pedicle screw device of claim 7, further comprising a drive feature formed in a top portion of the locking member and an opening formed in a bottom portion of the collet member to permit a driver to pass through the collet member and into the drive feature of the locking member to threadably engage the locking member with the threaded head portion of the bone screw.

9. The pedicle screw device of claim 7, wherein the plurality of protruding tabs are spaced apart and aligned around a circumference of the next portion of the bone screw member.

10. The pedicle screw device of claim 9, further comprising one or more locking tabs that are distanced from each other by a groove or opening.

11. The pedicle screw device of claim 10, wherein one or more of the locking tabs has an inner surface configured to engage with one or more of the protruding tabs to prevent counter-rotation of the locking member about the bone screw member.

12. The pedicle screw device of claim 7, wherein a set screw threadably engages with the internal thread portion of the tulip member and compresses the collet member towards the locking member to direct the locking member towards the base portion of the tulip member to lock the head assembly.

13. A pedicle screw tulip head assembly, comprising:
a tulip member having an internal thread portion, a base portion formed with a locking member aperture, a locking member socket, and one or more connector receiving holes;
a locking member substantially corresponding in shape to the locking member socket of the tulip member and comprising a top portion with a drive feature configured to receive a driver tool and a bottom portion with an expandable aperture;
a collet member formed with an opening enabling access to the locking member drive feature and one or more connector slots; and
one or more connectors insertable into the connector receiving holes of the tulip member and the connector slots of the collet member to connect the tulip member to the collet member to prevent rotation of the collet member within the tulip member.

14. The pedicle screw tulip head assembly of claim 13, wherein the locking member is substantially globular.

15. The pedicle screw tulip head assembly of claim 13, wherein the expandable aperture comprises one or more grooves disposed between two or more locking tabs, each locking tab comprising at least one face configured to engage with a portion of a bone screw member to prevent the locking member from counter-rotating with respect to the bone screw member.

16. The pedicle screw tulip head assembly of claim 15, wherein the at least one face of the locking member locking tabs abuts a portion of one or more protruding tabs extending from the bone screw member to prevent counter-rotation of the locking member with respect to the bone screw.

17. The pedicle screw tulip head assembly of claim 16, wherein each of the protruding tabs has at least one perpendicular face.

18. The pedicle screw tulip head assembly of claim 13, wherein a set screw threadably engages with the internal thread portion of the tulip member and compresses the collet member towards the locking ball to direct the locking ball towards the base portion of the tulip member to lock the head assembly in a fixed position relative to the bone screw member.

19. The pedicle screw tulip head assembly of claim 13, wherein an exterior side wall of the tulip member of the head assembly is connected to a rod retaining assembly comprising a tulip component and a collet component configured to retain a rod element.

20. The pedicle screw tulip head assembly of claim 19, wherein the locking member secures the tulip head assembly to a bone screw and a set screw threadably engages with one or more internal threads of the rod retaining assembly tulip component to secure a rod in a rod aperture of the collet component.

* * * * *